(12) United States Patent
Mayumi et al.

(10) Patent No.: US 6,875,448 B1
(45) Date of Patent: Apr. 5, 2005

(54) METHOD OF INTRACELLULAR SUSTAINED-RELEASE OF DRUG AND PREPARATIONS

(75) Inventors: Tadanori Mayumi, Hyogo (JP); Shinsaku Nakagawa, Osaka (JP); Yasuo Tsutsumi, Osaka (JP); Mahito Nakanishi, Osaka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/070,252

(22) PCT Filed: Mar. 3, 2000

(86) PCT No.: PCT/JP00/01267

§ 371 (c)(1),
(2), (4) Date: Jul. 8, 2002

(87) PCT Pub. No.: WO01/17511

PCT Pub. Date: Mar. 15, 2001

(30) Foreign Application Priority Data

Sep. 3, 1999 (JP) ............................................ 11/249845

(51) Int. Cl.$^7$ ......................... A61K 9/122; A61K 1/127
(52) U.S. Cl. ....................... 424/468; 424/450; 435/458; 435/320.1
(58) Field of Search ................................ 424/468, 450; 435/320.1, 458, 455; 514/44

(56) References Cited

U.S. PATENT DOCUMENTS

| | | | | |
|---|---|---|---|---|
| 5,631,237 A | * | 5/1997 | Dzau et al. | 514/44 |
| 5,820,879 A | * | 10/1998 | Fernandez | 424/450 |
| 2002/0064520 A1 | * | 5/2002 | Rozenberg | 424/93.2 |

FOREIGN PATENT DOCUMENTS

| | | | |
|---|---|---|---|
| JP | 09-110678 | | 4/1997 |
| JP | 11-116499 | | 4/1999 |
| WO | WO 97/04747 | * | 2/1997 |

OTHER PUBLICATIONS

H. Mizuguchi et al., "Application of Fusogenic Liposomes Containing Fragment A of Diphtheria Toxin to Cancer Therapy", *British Journal of Cancer*, 1996, pp. 472–476, vol. 73.

* cited by examiner

*Primary Examiner*—Dave Trong Nguyen
(74) *Attorney, Agent, or Firm*—Browdy and Neimark, P.L.L.C.

(57) ABSTRACT

A substance of interest is contained in nanospheres which are then encapsulated in fusogenic liposomes to prepare transport carriers that allow physiologically active substances, especially those having high molecular weight such as proteins and genes, to be introduced into cells efficiently and which permit the introduced active substance to be released in the cell at controlled rate. The fusogenic liposomes are prepared by conferring the fusogenic capability of Sendai virus to known liposomes.

9 Claims, 2 Drawing Sheets

METHOD OF INTRACELLULAR SUSTAINED-RELEASE OF DRUG AND PREPARATIONS

TECHNICAL FIELD

This invention relates to the technology of introducing drugs, proteins, genes and other physiologically active substances directly into cells and then allowing the introduced physiologically active substances to be released slowly in the cells. More particularly, the invention relates to a composition containing a physiologically active substance of interest which can be introduced directly into a cell and which thereafter can be released slowly in the cell. The invention also relates to a method for allowing the physiologically active substance of interest to be directly introduced cells and then released slowly in the cells.

BACKGROUND ART

For successful gene therapy and treatment with novel vaccines, efforts are being made today in order to ensure that biopolymers such as genes and antigenic proteins are introduced into the cytoplasm directly and efficiently. Unlike low-molecular weight drugs, high-molecular weight substances such as genes, antigenic proteins and physiologically active proteins are not only low in membrane permeability, absorption and tissue migration but they also undergo rapid degradation in blood. It has been desired to develop a technology by which those polymeric, physiologically active substances can be introduced into the cytoplasm in a desired and efficient manner without causing damage to the cell.

Liposomes can hold a number of substances and are still biocompatible, so they have drawn researchers' attention as carriers for transporting physiologically active substances. However, with liposomes, the efficiency of introducing the desired substance into a cell is sow low that it can hardly be introduced into the cytoplasm. To deal with this difficulty, various proposals have been made, including modifying the surfaces of liposomes with lectins, antibodies, etc. so that they are positively bound to cell surfaces. In fact, however, liposomes, whether surface-modified or not, are taken up by cells via endocytosis, so they are lysed by an enzyme called lysozyme and the proportion in which the substance of interest is actually transferred into the cytoplasm is at an extremely low level.

It was reported that in order to overcome this difficulty, fusogenic liposomes having the fusogenic capability of Sendai virus were developed as carriers that could be directly introduced into the cytoplasm via the cell membrane. Such fusogenic liposomes can be prepared by forming a complex between a liposome and the coat protein of Sendai virus which mediates fusion to the cell membrane. The prepared fusogenic liposomes have an almost comparable fusogenicity to Sendai virus and it has been reported that by encapsulating genes, proteins or other high-molecular weight substances, the substance of interest can be directly introduced into the cytoplasm with high efficiency but without causing cell injury ["DDS", Journal of the Japan Society of DDS, Vol. 13, No. 1, January 1998, pp. 21–26 and 27–33].

Even if the fusogenic liposomes are used as carriers for physiologically active substances, the release of the physiologically active substance in cells cannot be controlled, so the substance introduced into the cell is released at a time and its activity (toxicity) is not sustained. Take, for example, the case of introducing a gene into the cytoplasm; the gene is decomposed in the cytoplasm and its expression is not sustained. In the case of a protein having pharmacological activity, the activity is not sustained and it has to be administered by an increased number of times in a larger dose. Therefore, if physiologically active substances are introduced into cells directly and efficiently and if their release is controlled within the cytoplasm, the intended physiological activity can be exhibited efficiently in the cell. It is desired to develop a transport carrier that permits a substance of interest to be introduced into cells and which enables slow release of the substance in the cell.

Desired is the development of a safe and stable transport carrier that allows physiologically active substances, in particular high-molecular weight substances such as proteins and genes, to be introduced into cells efficiently and without damaging the cell membrane and which still can control and adjust the release profile of the introduced substance within the cell.

DISCLOSURE OF THE INVENTION

The present inventors paid particular attention to nanospheres currently developed as a technique for controlled release of drugs and accomplished the present invention by combining nanospheres with fusogenic liposomes.

Active efforts have heretofore been made in an attempt to achieve controlled in vivo release of drugs and this has spawned a number of techniques including the nanosphere technology. Nanospheres as contemplated in the invention are vesicles that are typically made of polymeric matrices and which encapsulate a large volume of drugs or high-molecular weight substances. The rate for the release of the trapped drug can be controlled by the appropriate choice for parameters including the size of the nanospheres, the type of the matrix-forming polymer, and the degree of crosslinking within or between molecules of the polymer. However, given alone, nanospheres are not easily taken up by cells and even if they are, the uptake is by endocytosis and the efficiency of introduction is very low because of lysis by the enzyme called lysozyme. The present inventors assumed that by combining fusogenic liposomes with nanospheres encapsulating a physiologically active substance of interest, it would be possible to achieve efficient introduction of the nanospheres into the cytoplasm while controlling the release of the encapsulated physiologically active substance within the cytoplasm. Based on this assumption, the inventors continued their studies and finally accomplished the present invention.

The present invention is characterized in that nanospheres encapsulating drugs, proteins, genes or other physiologically active substances are in turn encapsulated in liposomes to which is conferred the fusogenic capability of Sendai virus. Thus, the invention provides a method by which the physiologically active substances are not only introduced into cells directly and efficiently but are also released slowly in the cytoplasm. The invention also provides a composition to be used to implement the method.

MODES FOR CARRYING OUT THE INVENTION

Figure 1:
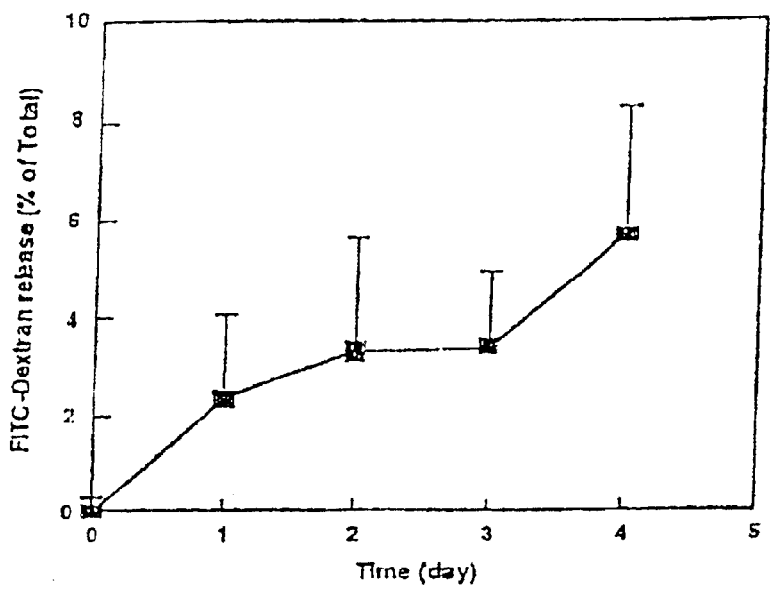
FIG. 1 is a graph showing the time profile of the release of FITC-dextran from the poly(lactic acid) nanospheres prepared in Example 2.

The nanospheres to be used in the invention may be prepared from any conventionally known materials by any conventionally known methods as long as they fit the purpose of the invention. See, for example, Leelarasamee N. et al., J. Microencapsul. 5; 147–57.1988; Singh M. et al., Pharm. Res. 12; 1796–1800, 1995; Rutledge L. C. et al., J. Am. Mosq. Dontrol. Assoc. 12; 39–44, 1996; Li J. K. et al., J. Pharm. Sci. 86; 891–895, 1997; and Kofler N. et al., Int. Arch. Allergy. Immunol. 113; 424–431, 1997. The nanospheres to be used in the invention have particle sizes of 10 nm–100 nm, preferably 20 nm–600 nm.

According to the invention, a desired physiologically active substance is encapsulated in nanospheres which, in turn, are encapsulated in fusogenic liposomes to prepare a composition which allows the physiologically active substance of interest to be introduced into cells and then released slowly in the cytoplasm. Liposomes can be used without any particular limitations as long as they can hold nanospheres and they can be prepared by conventional methods including reverse phase evaporation [Szoka, F. et al., Biochim. Biophys. Acta, Vol. 601 559 (1980)], injection of ether [Deamer, D. W., Ann. N.Y. Acad. Sci., Vol. 308 250 (1978)] or use of a surfactant [Bruner, J. et al., Biochim. Biophys. Acta, Vol. 455 322 (1976)].

Lipids to form liposome structures may be conventional ones including phospholipids, cholesterols and nitrogen lipids, and phospholipids are generally preferred. Exemplary phospholipids include various natural phopsholipids and their hydrogenation products, as well as synthetic phospholipids. These phospholipids may be used either alone or in admixture. If desired, cholesterols, stearylamines, alpha-tocopherols and other known additives for liposome formation may also be added during liposome formation.

Structurally, liposomes may be giant unilamellar vesicles (GUVs), large unilamellar vesicles (LUVs), multilamellar vesicles (MLVs) and small unilamellar vesicles (SUVs). The particle size of liposomes is varied as $\geq 1000$ nm for GUV, 100 nm–1000 nm for LUV, 200–5000 nm for MLV, and $\leq 100$ nm for SUV. For the purpose of the invention, the particle size is preferably about 10 nm–10 $\mu$m, more preferably 10–1000 nm.

Suitable lipids or mixed lipids as liposome formers, together with cholesterols as liposome forming additives, are dissolved in organic solvents such as tetrahydrofuran, chloroform and ethanol; after the mixture is put into a suitable vessel, the solvent is distilled off at reduced pressure to give a film of the liposome former on the inner surface of the vessel. In a typical case, a rotary evaporator is used to make a film of the lipid on the inner surface of a centrifugal tube. To the lipid film, a solution of nanospheres is added as an internal aqueous phase and mixed. The resulting liposome solution is reacted with a fusogenesis promoter such as Sendai virus, inactivated Sendai virus or a fusogenesis promoting protein to prepare fusogenic liposomes. Sendai virus is inherently nonpathogenic to humans but it is preferably illuminated with uv light so that the viral RNA is fragmented to ensure utmost safety. The fusogenic liposomes of the invention are safe particles since they differ from the starting liposomes only in that they have been conferred the fusogenic capability of Sendai virus. The fusogenic liposomes of the invention may typically be formed by the method of Bangham et al. (Bangham A. D., J. Mol. Biol., 13:238–252, 1965).

Examples of the physiologically active substance that can be encapsulated in the fusogenic liposomes of the invention include: various drugs that develop physiological actions when they are introduced into cells; physiologically active proteins such as hormones, lymphokines and enzymes: antigenic proteins that work as vaccines: genes such as those which are expressed in cells, plasmids, and genes that are involved in the expressing of specified genes that induce expression; as well as various genes and antisenses that are introduced for gene therapy. The technology of the invention is suitably applied to physiologically active substances of high molecular weight such as proteins and genes but they can also be applied to various low-molecular weight drugs to give preferred results.

Safety is not the only feature of the fusogenic liposomes of the invention; they are also highly stable and are easy to handle. According to the method of the invention, a desired substance can be efficiently introduced into the cytoplasm without causing injury to the functions of the cell membrane which is the barrier to the ingress of substances into the cytoplasm. By the appropriate choice for the characteristics of nanospheres such as the starting materials, particle size and the degree of crosslinking, the profile of the release of the introduced active substance in the cytoplasm can be controlled and, in particular, its slow release can be realized to attain the principal object of the invention. In addition, physiologically active substances can be introduced into animals by contacting viable cells with the fusogenic liposomes of the invention.

The following reference example and working examples are provided for further illustrating the present invention but are in no way to be taken as limiting.

REFERENCE EXAMPLE

Materials in Experiment

Reagents, L-α-dimyristoylphosphatidic acid, egg yoke phosphatidylcholine (PC) and chloroform, were purchased from NOF CORP.; cholesterol, sucrose, p-phenylene diamine and calcium ionophore were purchased from Wako Pure Chemical Industries, Ltd.; carboxy-modified 0.02-$\mu$m yellow green fluorescent fluospheres, carboxy-modified 0.02-nm red fluorescent fluospheres (nanospheres) and calcium green-1 acetoxymethyl derivative were purchased from Molecular Probes, Inc.; and Eagle's MEM was purchased from Nissui Pharmaceutical Co., Ltd.

Methods of Experiment

<Preparation and Purification of Liposomes and Fusogenic Liposomes>

Liposomes were prepared by a partial modification of the method of Bangham et al., supra. Mixed lipids (12.72 mg) [PA:PC:Chol=1:4:5 (molar ratio)] were suspended in chloroform and a lipid film was prepared on the inner surface of a centrifugal tube using a rotary evaporator. To the lipid film, 300 $\mu$L of a nanosphere/BBS (–) solution was added as an internal aqueous phase and the two phases were mixed by vortexing to prepare liposomes. By shaking at 37° C. for 2 hours, the solution of the liposomes was reacted with Sendai virus to prepare fusogenic liposomes. To purify the fusogenic liposomes, the reaction solution was layered onto a 6%, 20%, 30%, 40% and 50% sucrose density gradient and centrifuged at 24000 rpm and 4° C. for 2 hours (SW28.1, Beckman). After centrifugation, the fusogenic liposome fractions at the 20%–30% and 30%–40% sucrose interfaces were recovered and washed with BSS(−) [20000 rpm, 4° C.×40 minutes (SW28.1, Beckman)]. Before use in the experiment, the fusogenic liposomes were illuminated with uv light (2000 J/m$^3$) in order to fragment the RNA of Sendai virus.

<R18 labelling of liposomes and fusogenic liposomes>

A portion (0.1 mM) of R18/ethanol solution was added in a 1/100 volume to the liposomes or fusogenic liposomes were conditioned to have the same fluorescence intensity of 150000 (Ex, 490 nm; Em, 515 nm) and reaction was performed at room temperature for 1 hour. The unreacted R18 was removed by centrifuging at 25000 rpm and 4° C. for 40 minutes (SW55, Beckman).

<Cultured cells>

Mouse fibroblast cells Ltk$^-$ were cultured in an Eagle's MEM medium containing 10% fetal calf serum (FCS).

<Introducing Nanospheres Into Cultured Cells>

$4\times10^4$ Ltk$^-$ cells were seeded on a 4-well chamber slide. After one day, the cells were washed with PBS(−) and exposed for 1 minute to the action of the nanospheres, liposomes or fusogenic liposomes (fluorescence intensity, 100000; Ex, 490 nm; Em, 515 nm). After washing with PBS(−), 0.1% p-phenylenediamine/Eagle's MEM medium was added as an anti-stain agent.

<Examination by Confocal Laser Microscopy>

Examination was made with a confocal laser scanning fluorescence microscope, MRC-1024 (BIO-RAD). After excitation with a Kr/Ar laser, the nanospheres (yellow green fluorescent) were examined at Ex of 488 nm and Em of 540 nm (540 DF) and R18 was examined at Ex of 568 nm and Em of 585 nm (585 LP).

<Measuring the Efficiency of Introduction Into Cells With the Aid of $Ca^{2+}$ Indicator>

To the nanospheres (red fluorescent), calcium green-1 acetoxymethyl derivative was added as a fluorescent $Ca^{2+}$ indicator to give a concentration of 20 mM and mixed at room temperature for 1 hour so that it was adsorbed on the nanospheres. The unadsorbed calcium green-1 was removed by dialysis (Spectra/Por Membranes MWCO:12–14000) and buffer replacement was performed to prepare liposomes and fusogenic liposomes. $2\times10^5$ Ltk$^-$ cells that had been seeded on 6-well plates one day before were washed with PBS(−) and exposed for 1 minute to the action of the calcium green-1 acetoxymethyl derivative, calcium green-1 adsorbed nanospheres, liposomes or fusogenic liposomes which were all conditioned to have the same fluorescence intensity of 2700 (Ex. 488 nm; Em, 534 nm). Thereafter, the cells were washed with PBS(−), cultured in an Eagle's MEM medium for 1 hour, stripped from the medium with trypsin and subjected to the measurement of fluorescence intensity (Ex, 488 nm; Em, 534 nm). Thereafter, a calcium ionophore/DMSO solution was added to give a concentration of 0.1 mg/mL and fluorescence intensity was measured at Ex=488 nm and Em=534 nm.

Results and Discussion

To begin with, the fluorescence labelled nanospheres having a diameter of 20 nm were examined with a confocal laser microscope at a magnification of 10000 in order to see whether they could be encapsulated in the liposomes or fusogenic liposomes. As a result, aggregated images were obtained but the fluorescence of the 20-nm$^4$ nanospheres was observed only in the positions on transmission micrographs where the liposomes or fusogenic liposomes were observed. Thus, it became clear that the nanospheres could be encapsulated into liposomes and that using such liposomes, one could prepare fusogenic liposomes having the nanospheres encapsulated therein. It was confirmed that several nanospheres had been encapsulated in each liposome or fusogenic liposome.

The thus prepared fusogenic and non-fusogenic liposomes having the nanospheres encapsulated therein were labelled with R18 and the efficiency of nanosphere introduction into Ltk$^{31}$ cells was determined. Fluorescence was hardly detectable in the cells on which the non-fusogenic, nanosphere encapsulating liposomes or the nanospheres alone were acted upon; on the other hand, a large number of nanospheres were introduced into the cells on which the fusogenic liposomes had been acted. Unlike the nanospheres, the distribution of the red fluorescence from R18 used as the marker of the fusogenic liposomes was not observed within the cells but observed on the cell membrane. Section images of the Ltk$^{31}$ cells on which the fusogenic liposomes had been acted were successively taken in thicknesses of 4 μm as calculated from the surface of attachment; nanospheres were clearly visible inside the cell membrane in conformity with the cell shape, indicating the presence of R18 fluorescence on the cell membrane. Thus, the fusogenic capability of the fusogenic liposomes was reconfirmed and it was suggested that even the nanospheres in suspension could be efficiently introduced into the cytoplasm by using the fusogenic liposomes.

These phenomena were further studied using a calcium green-1 acetoxymethyl derivative as a $Ca^{2+}$ indicator. The calcium green-i acetoxymethyl derivative does not emit fluorescence on its own but when in a cell, it is hydrolyzed by an endogenous esterase to form a chelate with $Ca^{2+}$, whereupon it emits strong fluorescence. Using this nature of the calcium green-1 acetoxymethyl derivative, the present inventors prepared nanospheres having said derivative adsorbed on the surface. The nanospheres were then encapsulated into fusogenic liposomes and the efficiency of introduction of the nanospheres into the cytoplasm was evaluated. In substantial absence of calcium in the cytoplasm, fluorescence was hardly detectable in each of the groups under test. Even when the intracellular calcium concentration was elevated by the action of calcium ionophore, no fluorescence was detected in the cells on which the nanospheres alone or the nanosphere-encapsulating, non-fusogenic liposomes had been acted. Fluorescence was barely detectable in the cells on which was acted the calcium green-1 acetoxymethyl derivative alone as it was passively transported into the cytoplasm. However, the cells treated with the nanosphere-encapsulating, fusogenic liposomes emitted at least 20 times as much fluorescence as the cells treated solely with the calcium green-1 acetoxymethyl derivative, thus demonstrating the ability of the fusogenic liposomes to permit efficient and positive introduction of nanospheres into the cytoplasm.

These results show that using the fusogenic liposomes, 20-nm$^\oplus$ nanospheres were directly introduced into the cytoplasm with a very high efficiency. The results also show that using the fusogenic liposomes, not only molecules but also vesicles could be introduced into the cytoplasm. It is therefore shown that the fusogenic liposomes can achieve not only spatial dynamic control of substances within cells but also temporal dynamic control such as slow release of drugs from the vesicles introduced into the cell.

EXAMPLE 1

Fusogenic Liposome Assisted Introduction of Rhodamine-PE Encapsulating Polyurea Nanospheres and FITC-Dextran Encapsulating Poly (lactic acid) Nanospheres into the Cytoplasm It was found in the Reference Example that using the fusogenic liposomes, even the nanospheres or vesicles having a diameter of 20 nm could be efficiently introduced into the cytoplasm. Based on this finding, the present inventors prepared nanospheres capable of slow release of drugs, attempted to introduce them into the cytoplasm and checked for their stability in the cell. Two models were prepared for the future nanospheres capable of slow release of drugs into the cytoplasm; one was polyurea nanospheres encapsulating rhodamine-PE as a fat-soluble drug model and the other was poly(lactic acid) nanospheres (PLA nanospheres) encapsulating FITC-dextran as a model for a drug in aqueous solution.

These two kinds of nanospheres were encapsulated in fusogenic liposomes. After allowing the liposomes to act on cells, their stability in the cell was examined by confocal laser microscopy.

Materials in Experiment

Diacyl phosphatidylethanolamine-N-lissamine rhodamine B sulfonyl (rhodamine-PE) was purchased from Avanti Polar Lipods, INc. Polyvinyl alcohol (PVA), tolylene diisocyanate (TDI), soybean oi, poly(lactic acid) (MW= 5000; PLA), Span 80 and methylene chloride were purchased from Wako Pure Chemical Industries, Ltd. FITC-Dextran (MW=150000) was purchased from Sigma. Other reagents were the same or substantially the same as those described in the Reference Example (see under "Materials in Experiment").

Methods of Experiment

<Preparing Rhodamine-PE Encapsulating Polyurea Nanospheres (Ph-Polyurea Nanospheres)>

The Ph-polyurea nanospheres were prepared by interfacial polymerization as follows. A portion (20 mL) of 0.5% PVA/$H_2O$ was homogenized at 20000 rpm; a mixture of TDI (2.4 g), soyben oil (2.5 g) and rhodamine-PE (0.5 mg/500 mL) was added slowly and homogenized for 3 minutes to prepare an oil-in-water (O/W) emulsion. Another portion (100 mL) of 0.5% PVA/$H_2O$ was homogenized at 10000 rpm and the previously homogenized mixture was added slowly and homogenized for an additional 10 minutes to prepare an oil-in-water-in-water [(O/W)/W] emulsion. To reinforce the surfaces of the nanospheres, 100 mL of 0.5% PVA/$H_2O$ was added and homogenized for 20 minutes, then homogenized at 7000 rpm for 2 hours to prepare Rh-polyurea nanospheres. To purify, the polyurea nanospheres were layered onto a 10%, 20%, 30%, 40% and 50% sucrose step density gradient and centrifuged at 24000 rpm for 2 hours (SW28.1, Beckman). The Rh-polyurea nanosphere fraction at the the 30%–40% sucrose interface was recovered and used in the experiment.

<Preparing FITC-Dextran Encapsulating PLA Nanospheres (FITC-PLA Nanospheres)>

The FITC-PLA nanospheres were prepared by interfacial precipitation as follows. One gram of PLA and 1 mL of Span 80 were added to 30 mL of $CH_3Cl_2$ and homogenized at 10000 rpm; 5 mL of FITC/dextran (100 mg/mL) was added slowly and homogenized for 1 minute to prepare a water-in-oil (W/O) emulsion; this emulsion was slowly added to 100 mL of 0.5% PVA/$H_2O$ and homogenized for an additional 5 minutes to prepare a water-in-oil-in-water [(W/O)/W] emulsion. The emulsion was further homogenized at 7000 rpm for 1 hour to prepare FITC-PLA nanospheres which were purified by sucrose step density-gradient centrifugation. The FITC-PLA nanosphere fractions at the 0–10% and 10–20% sucrose interfaces were recovered and used in the experiment.

<Preparing and Purifying Fusogenic Liposomes>

Liposomes and fusogenic liposomes were prepared by a modification of the procedures described in the Reference Example (see under "Preparing and purifying liposomes and fusogenic liposomes" in "Methods of Experiment"). In the preparation of Rh-polyurea nanosphere encapsulating fusogenic liposomes, the method of Bangham et al. was repeated, with the fluorescence intensity of the nanospheres being adjusted to 50000 (Ex, 550 nm; Em, 590 nm), to prepare liposomes. Thereafter, the liposome solution was layered onto a 10%, 20%, 30%, 40% and 50% sucrose density gradient and centrifuged at 24000 rpm for 2 hours (SW28.1, Beckman); the fraction at the 20–30% sucrose interface was recovered and the liposomes were purified. The purified liposomes were reacted with Sendai virus and the reaction product was layered onto a 20%. 30%, 35%, 45% and 50% sucrose density gradient and centrifuged at 24000 rpm for 2 hours (SW28.1, Beckman): the fractions at the 30–35% and 35%–40% sucrose interfaces were recovered to give a purified form of Rh-polyurea nanosphere encapsulating fusogenic liposomes.

In the preparation of FITC-PLA nanosphere encapsulating fusogenic liposomes, liposomes were first prepared, with the fluorescence intensity of the nanospheres being adjusted to 10000 (Ex, 490 nm; Em, 529 nm). The liposomes were reacted with Sendai virus and the reaction product was layered onto a 10%, 20%, 30%, 40% and 50% sucrose density gradient and centrifuged at 24000 rpm for 2 hours (SW28.1, Beckman). The fusogenic liposomes prepared from the nanospheres recovered from the fractions at the 0–10% and 10–20% sucrose interfaces were present at the 10–20% and 20%–30% sucrose interfaces, respectively; these fractions were recovered to give a purified form of FITC-PLA nanosphere encapsulating fusogenic liposomes.

<Introducing Nanospheres Into Cultured Cells>

$4 \times 10^4$ Ltk$^-$ cells were seeded on 4-well chamber slides. After one day, the cells were washed with PBS(−) and exposed for 1 hour to the action of the Rh-polyurea nanospheres, Rh-polyurea nanosphere encapsulating fusogenic liposomes (fluorescence intensity, 10000; Ex, 550 nm; Em. 590 nm), FITC-PLA nanospheres, and FITC-PLA nanosphere encapsulating fusogenic liposomes (fluorescence intensity, 700: Ex, 490 nm: Em, 520 nm). After washing with PBS(−), the cells were cultured in an Eagle's MEM medium. After one day, the medium was replaced by an anti-stain agent, or a 0.1% p-phenylenediamine/Eagle's MEM medium and the cells were examined.

<Examination by Confocal Laser Microscopy>

Examination was made in accordance with the procedure described in the Reference Example (see under "Examination by confocal laser microscopy" in "Methods of Experiment"). For rhodamine-PE, the conditions were Ex of 568 nm and Em of 585 nm (585 LP); for FITC-dextran, the conditions were Ex of 488 nm and Em of 540 nm (540 DF). The prepared Rh-polyurea nanospheres and FITC-PLA nanospheres, as well as the fusogenic liposomes encapsulating the RH-polyurea nanospheres and the fusogenic liposomes encapsulating the FITC-PLA nanospheres were examined by confocal laser microscopy; without doubt, the two kinds of nanospheres were prepared.

The fluorescence of the substances encapsulated in the two kinds of nanospheres occurred in the positions on transmission micrographs where the fusogenic liposomes were observed. Thus, it became clear that the polyurea nanospheres and PLA nanospheres could be encapsulated into fusogenic liposomes. According to the transmission photographs, the polyurea nanospheres prepared in Example 1 had particle sizes of about 200 nm and the PLA nanospheres had particle sizes of about 500 nm. These nanospheres were encapsulated in the fusogenic liposomes, indicating that even fairly large nanospheres could be encapsulated in the fusogenic liposomes. Since the polyurea nanospheres could be encapsulated in the fusogenic liposomes, it became clear that according to the invention, one could produce fusogenic liposomes that encapsulated a large volume of hydrophobic drugs which had been encapsulated with only low efficiency by the conventional methods of liposome preparation. An examination made one day after the nanosphere encapsulating fusogenic liposomes were allowed to act on the Ltk$^-$ cells offered positive evidence for the presence of the nanospheres within the cells. The Ltk$^-$ cells into which the nanospheres were introduced by means of the fusogenic liposomes showed no morphological changes after the lapse of one day and this indicates the absence of superficial cell injury.

These results show that the fusogenic liposomes can introduce 100–500 nm nanospheres into the cytoplasm and that the introduced nanospheres remain stable in the cytoplasm even after the passage of a day. Based on this finding, the inventors studied the release of drugs from the nanospheres in Example 2.

EXAMPLE 2

Slow Drug Release from FITC-Dextran Encapsulating Poly(lactic acid) Nanospheres

It was found in Example 1 that the prepared nanospheres could be introduced into the cytoplasm by means of the fusogenic liposomes and that they remained stable within the cell for at least 24 hours. However, if these nanospheres are incapable of releasing drugs at slow rate, it is of course impossible to have drugs released slowly in cells. The present inventors therefore chose FITC-dextran as a model drug and conducted an experiment to evaluate its slow releasability from the prepared FITC-PLA nanospheres.

Materials in Experiment

The reagents were the same or substantially the same as those described in Example 1 (see under "Materials in Experiment").

Methods of Experiment
<Evaluating the Slow Release of Drug From FITC-Dextran Encapsulating PLA Nanospheres>

The FITC-PLA nanospheres were suspended in BSS(–) at a fluorescence intensity of 100000 (Ex, 490 nm; Em, 520 nm) and incubated at 37° C. At days 0, 1, 2, 3 and 4, centrifuge was conducted at 10000 rpm to remove the nanospheres and the amount of FITC-dextran in the supernatant was measured with a fluorescence photometer at Ex of 490 nm and Em of 520 nm.

Results and Discussion

The release of FITC-dextran from the FITC-PLA nanospheres prepared in Example 1 was observed. As FIG. 1 shows, the FITC-dextran was released in only about 6% even at day 4 and its slow release was evident. The PLA nanospheres or microspheres are generally said to release drugs over a period from about 3 weeks to three months and in one report, the release was ten-odd percent at day 3. Compared to the data reported previously, the PLA nanospheres prepared in Example 1 allow for somewhat slower drug release. However, the rate of drug release from the PLA nanospheres can be controlled by adjusting the molecular weight of PLA and the size of spheres, so the slow release characteristics of drugs in the cytoplasm can be controlled by appropriately changing the conditions of nanosphere preparation.

Considering the result of Example 2 in combination with that of Example 1, it is concluded that the nanospheres allowed the drug to be slowly released in the cytoplasm.

EXAMPLE 3

Studies on the Stabilization and Controlled Release of Plasmid DNA Encapsulated in Gelatin Nanospheres The T7 expression system enables efficient gene expression if bacteriophage T7 RNA polymerase and plasmid DNA having the T7 promoter sequence are both present in the cytoplasm. However, due to the low stability of plasmid DNA in the cytoplasm, gene is rapidly decomposed away, leading to only a very brief period of gene expression. Therefore, in order for the T7 expression system to express genes in therapeutically necessary amount for the necessary period, the genes in the cytoplasm must be controlled dynamically by stabilizing the plasmid DNA in the cytoplasm and allowing it to be released slowly. Nanospheres are used as formulations capable of slow release of drugs and as shown in the Reference Examples and Examples 1 and 2, they can not only be introduced into but can also be released slowly in the cytoplasm. While nanospheres can be made of various materials including PLA mentioned in Example 1, gelatin has particularly good biocompatibility and can easily form gelatin nanospheres by coacervation with plasmid DNA and other high-molecular weight substances. For experimental purposes, gelatin nanospheres are considered to provide ease in evaluating the slow intracellular release of drugs using gene expression as a marker because the release pattern can be conveniently controlled by crosslinking and because the gelatin nanospheres permit faster drug release than the PLA nanospheres which are generally held to be capable of fast enough drug release. With these points taken into consideration, the gelatin nanospheres are believed to be most suitable for use at the first stage of applying the slow intracellular release to the T7 expression system. Therefore, in Example 3, gelatin nanospheres containing plasmid DNA were prepared by phase separation and studies were made on their ability to stabilize plasmid DNA, as well as the control of its release.

Materials in Experiment

Gelatin (type A, produced from porcine skin) was purchased from Sigma. Other reagents, 2-morpholinoethanesulfonic acid monohydrate (MES), 1-ethyl-3(3-dimethylaminopropyl)-carbodiimide hydrochloride (EDC, WSC), $Na_2SO_4$ and glycine were purchased from Wako Pure Chemical Industries, Ltd. Pentobarbital was purchased from Dainippon Pharmaceutical Co., Ltd. The other reagents were the same or substantially the same as those described in the Reference Example (see under "Materials in Experiment").

Methods of Experiment

<Preparing pT7-β-Globin-IRES-L-polyA Encapsulating Gelatin Nanospheres>

The pT7-β-globin-IRES-L-polyA encapsulating gelatin nanospheres were prepared by phase separation. A hundred milliliters of 5% gelatin solution and a 45 mM $Na_2SO_4$ solution containing pT7-β-globin-IRES-L-polyA(0.2 mg/mL) were mixed in a 1.5 mL Eppendorf tube and incubated in a water bath at 57° C. for 10 minutes. Thereafter, the mixture was vortexed for 1 minute, layered on top of a 35%, 55% and 66% sucrose density gradient and centrifuged at 19000 rpm and 20° C. for 1 hour (SW55, Beckman). A 55% sucrose layer containing the pT7-β-globin-IRES-L-polyA encapsulating gelatin nanospheres was recovered and subjected to the experiment.

<Crosslinking the Gelatin Nanospheres>

After preparing the gelatin nanospheres, the 55% sucrose layer was diluted 2-fold and reacted with an MES buffer solution (0.2 M MES, 0.1 or 0.5 mg/mL of EDC, pH 4.5) that was added in a 1/10 volume. Thirty minutes later, glycine was added to give 0.2 M, thereby quenching the reaction.

<Preparing Fraction S-9>

Wistar rats were fasted overnight, anesthetized with peritoneally administered pentobarbital and had the blood taken from the heart until death. Ice-cooled 0.15 M KCl was perfused through the portal vein into the liver in order to remove a maximum volume of the hepatic blood. The liver was extracted and washed with ice-cooled 0.15 M KCl; after adding ice-cooled 0.15 M KCl in an amount three times its weight, the liver was homogenized under cooling with ice. The homogenate was centrifuged at 9000 g and 4° C. for 10 minutes. The supernatant was used as fraction S-9. This fraction was quick frozen with liquid nitrogen and stored at −80° C.

<Studying the Stabilization of Plasmid DNA>

The pT7-β-globin-IRES-L-polyA encapsulating gelatin nanospheres were put into a 5% solution of fraction S-9 and reaction was performed at 37° C. After a specified time, the S-9 solution was removed by centrifuging and the remaining nanospheres were destroyed by treatment with trypsin; the plasmid DNA was stained with ethidium bromide and its stability was evaluated by agarose gel electrophoresis.

<Release of Plasmid DNA From Gelatin Nanospheres>

The pT7-β-globin-IRES-L-polyA encapsulating gelatin nanospheres were crosslinked at various concentrations by the method described above and treated in 1.25 mg/mL of trypsin for a specified time. Thereafter, the nanospheres were removed by centrifuging and the amount of plasmid DNA released was determined with DABA.

Results and Discussion

Figure 2:
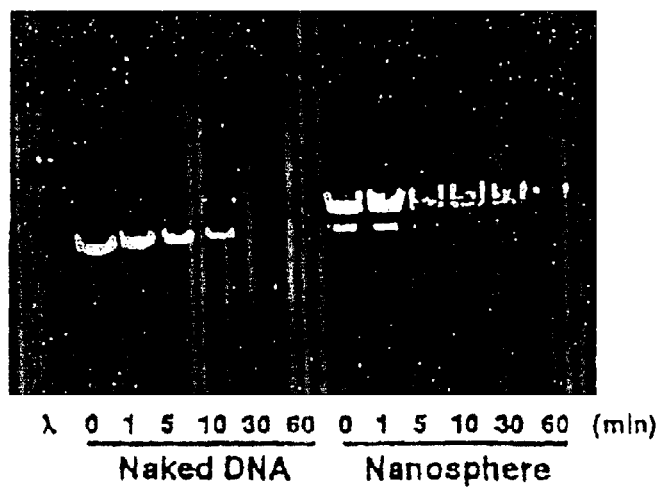
FIG. 2 is an agarose gel electrophoretogram showing how encapsulated plasmid DNA having the T7 promoter sequence remained stable in the gelatin nanospheres prepared in Example 3 as they were reacted with a rat liver homogenate.
Figure 3:
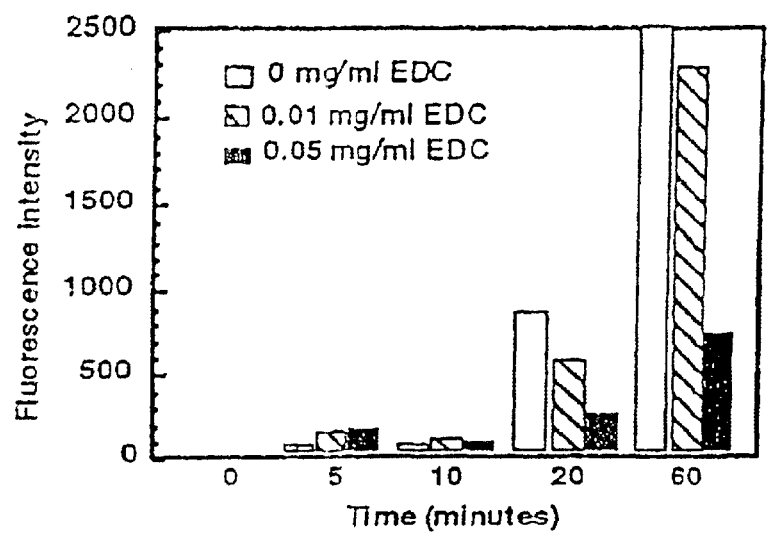
FIG. 3 is a graph showing the relationship between the degree of crosslinking of gelatin and the release of encapsulated plasmid DNA from the gelatin nanospheres prepared in Example 3.

In order to evaluate the stability of plasmid DNA in cells, the degradability of plasmid DNA was examined by agarose gel electrophoresis using fraction S-9 of the rat liver homogenate (FIG. 2). When the naked plasmid DNA was reacted with fraction S-9, it was substantially degraded within 30 minutes; on the other hand, when it was encapsulated within the gelatin nanospheres, the plasmid DNA remained stable at 60 minutes and thereafter. This showed that encapsulating plasmid DNA within nanospheres was effective in increasing its stability. According to the release pattern of plasmid DNA from the gelatin nanospheres in trypsin solution after treatment with various concentrations of the crosslinker, the release of plasmid DNA was suppressed by increasing the concentration of the crosslinker (FIG. 3).

In the T7 expression system which expresses genes in the cytoplasm where plasmid DNA tends to degrade faster than in the nucleus, the stability of the plasmid DNA in nanospheres and the rate of its release from them are two key factors in adjusting the amount and period of gene expression. The results of Example 3 suggest that the stability of plasmid DNA is improved by encapsulating them within gelatin nanospheres and that the rate of release of a drug (which is plasmid DNA in the experiment described above) can be controlled by altering the conditions of nanosphere preparation. This is evidence for the possibility of adjusting the amount and period of gene expression.

EXAMPLE 4

Gene Expression by Plasmid DNA Encapsulated in Gelatin Nanospheres Encapsulated in Fusogenic Liposomes In Example 3, it was shown that the intracellular stability of plasmid DNA was improved by encapsulating it in nanospheres and that the amount of release of plasmid DNA could be controlled by treating gelatin nanospheres with a crosslinker. Based on these results, the present inventors attempted to increase the period and amount of gene expression by the T7 expression system. To this end, in Example 4, gelatin nanospheres encapsulating PT7-β-globin-IRES-L-polyA which was a luciferase expressing plasmid DNA having the T7 promoter were encapsulated in fusogenic liposomes and introduced into T7 RNA polymerase producing cells to see how the plasmid DNA slowly released in the cell would affect the pattern of gene expression by the T7 expression system.

Materials in Experiment

As a luciferase assay system, PicaGene, a product of TOYO INK MFG. CO., LTD. was used. The other reagents were the same or substantially the same as those described in the Reference Example and Examples 1–3 (see under "Materials in Experiment").

Methods of Experiment

<Preparing and purifying fusogenic liposomes>

Fusogenic liposomes were prepared by a partial modification of the procedures described in the Reference Example (see under "Preparing and purifying liposomes and fusogenic liposomes"). To be specific, Sendai virus whose RNA was fragmented by illumination with uv light (2000 $J/m^2$) were reacted with liposomes to obtain fusogenic liposomes.

<Cultured Cells>

Monkey kidney epithelial cells LLC-MK2#10 were cultured in an Eagle's MEM medium containing 10% fetal calf serum (FCS).

<Introducing a Substance Into Cultured Cells>

$5 \times 10^4$ LLC-MK2#10 cells were seeded on 12-well plates. After one day, the cells were washed with PBS(−). In a separate step, pT7-β-globin-IRES-L-polyA encapsulating fusogenic liposomes, pT7-β-globin-IRES-L-polyA encapsulating gelatin nanosphere encapsulating fusogenic liposomes and pT7-β-globin-IRES-L-polyA encapsulating gelatin nanospheres were diluted in a serum-free Eagle's MEM medium at an appropriate concentration to incorporate the same amount of genes. Such fusogenic liposomes or nanospheres were allowed to act on the washed cells for 1 hour. After washing with PBS(−), the cells were cultured in an Eagle's MEM medium.

<Measuring the Luciferase Activity>

Luciferase activity was measured with the luciferase assay system and a luminometer (Lumit LB 9507, Berthold). The activity was expressed in terms of relative light unit/well.

For other methods of experiment, see "Methods of Experiment" in Example 3.

Results and Discussion

Figure 4:
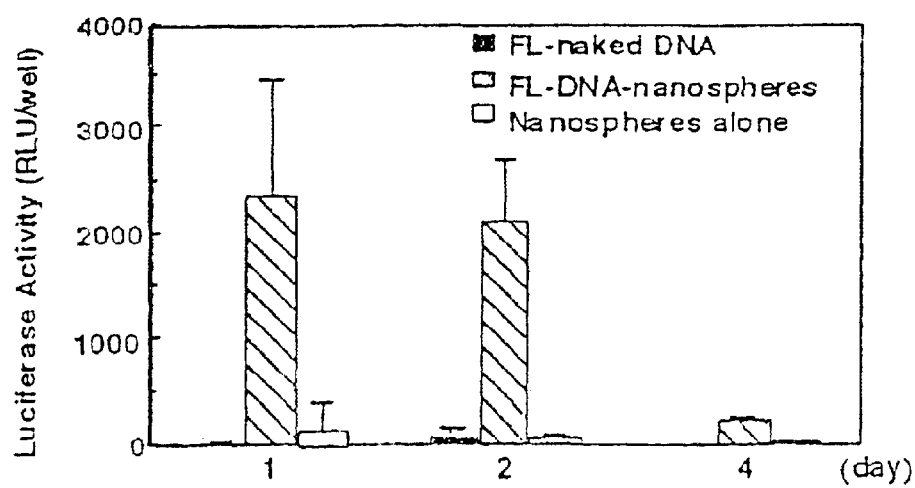
FIG. 4 is a graph showing the time profile of the intracellular expression of plasmid DNA having a T7 promoter that was encapsulated in gelatin nanospheres which in turn were encapsulated in the fusogenic liposomes of the invention.

The plasmid DNA containing nanospheres crosslinked with 0.01 mg/mL of EDC were encapsulated in the fusogenic liposomes, introduced into T7 RNA polymerase producing cells and checked for their effectiveness using the daily profile of gene expression as a marker (FIG. 4). The fusogenic liposomes encapsulating only plasmid DNA and the plasmid DNA encapsulating nanospheres, both having been processed to have the same amount of genes, were similarly allowed to act on the cells and the daily profile of luciferase activity was measured. The result was substantially nil. In the group treated with the fusogenic liposomes encapsulating the plasmid DNA encapsulating nanospheres, very high luciferase activity was observed at day 1 and day 2 after gene introduction. The efficiency of gene expression was substantially the same at day 1 and day 2 after gene introduction. The pattern of gene expression in the T7 expression system has been shown to be such that gene expression disappears significantly at day 1 of gene introduction, so the result of Example 4 seems to suggest that a certain extension of the period of gene expression could be achieved by incorporating a gene in nanospheres and introducing it into the cytoplasm. Under the conditions used in Example 4, the gene expression dropped at day 4. However, in Example 4, the efficiency of gene expression increased and the expressed gene remained stable for at least 2 days. Hopefully, the amount and period of gene expression can be adjusted by altering the conditions of nanosphere preparation.

What is claimed is:

1. A slow-release composition for introducing a physiologically active substance into the cytoplasm, comprising nanospheres that encapsulate the physiologically active substance and which are encapsulated in liposomes having fusogenic capability conferred by reaction with a Sendai virus.

2. The composition according to claim 1, wherein the nanospheres have a particle size of 10–600 nm.

3. A slow-release composition for introducing a physiologically active substance into the cytoplasm, comprising nanospheres that encapsulate the physiologically active substance and which are encapsulated in liposomes having fusogenic capability conferred by reaction with a Sendai virus, wherein the physiologically active substance is selected from the group consisting of low-molecular weight drugs, proteins and genes.

4. A process for producing a composition that contains a physiologically active substance and which allows it to be slowly released in the cytoplasm, comprising the steps of encapsulating a physiologically active substance in nanospheres and encapsulating said nanospheres in liposomes having fusogenic capability conferred by reaction with a Sendai virus.

5. A method of introducing a physiologically active substance into an animal by contacting a viable cell with the composition according to claim 1.

6. The composition according to claim 2, wherein the physiologically active substance is selected from the group consisting of low-molecular weight drugs, proteins and genes.

7. A method of introducing a physiologically active substance into an animal by contacting a viable cell with the composition according to claim 2.

8. A method of introducing a physiologically active substance into an animal by contacting a viable cell with the position according to claim 3.

9. A method of introducing a physiologically active substance into an animal by contacting a viable cell with the composition according to claim 6.

* * * * *